US012605524B2

(12) United States Patent
Gilbert et al.

(10) Patent No.: US 12,605,524 B2
(45) Date of Patent: Apr. 21, 2026

(54) DEVICE FOR CLEAN CATHETERIZATION

(71) Applicants:Catherine Gilbert, New Orleans, LA (US); Jorge Nagel, New Orleans, LA (US)

(72) Inventors: Catherine Gilbert, New Orleans, LA (US); Jorge Nagel, New Orleans, LA (US)

( * ) Notice: Subject to any disclaimer, the term of this patent is extended or adjusted under 35 U.S.C. 154(b) by 12 days.

(21) Appl. No.: 17/725,548

(22) Filed: Apr. 21, 2022

(65) Prior Publication Data

US 2022/0339405 A1 Oct. 27, 2022

Related U.S. Application Data

(60) Provisional application No. 63/177,505, filed on Apr. 21, 2021.

(51) Int. Cl.
*A61M 25/01* (2006.01)
*A61M 25/00* (2006.01)

(52) U.S. Cl.
CPC ..... *A61M 25/0111* (2013.01); *A61M 25/0017* (2013.01); *A61M 25/0029* (2013.01); *A61M 2025/0024* (2013.01); *A61M 2205/273* (2013.01); *A61M 2207/10* (2013.01)

(58) Field of Classification Search
CPC .......... A61M 25/0111; A61M 25/0017; A61M 25/0029; A61M 2025/0024; A61M 2205/273; A61M 2207/10
See application file for complete search history.

(56) References Cited

U.S. PATENT DOCUMENTS

| | | | |
|---|---|---|---|
| 2011/0213303 A1* | 9/2011 | Lentz ................. | A61M 25/005 604/524 |
| 2015/0112314 A1* | 4/2015 | Gustavsson ....... | A61M 25/0017 264/250 |
| 2016/0270692 A1* | 9/2016 | Johnson .............. | A61B 5/0836 |
| 2018/0071486 A1* | 3/2018 | O'Flynn ........... | A61M 25/0017 |
| 2021/0146114 A1* | 5/2021 | Grant ................ | A61M 39/0208 |
| 2021/0252255 A1* | 8/2021 | Jewett ............... | A61M 25/0119 |
| 2022/0072276 A1* | 3/2022 | Fominas ........... | A61M 25/0111 |

* cited by examiner

*Primary Examiner* — Rebecca E Eisenberg
*Assistant Examiner* — Kate Elizabeth Strachan
(74) *Attorney, Agent, or Firm* — David M. Stein

(57) ABSTRACT

A device for catheterization is disclosed. Such a device includes a hollow catheter, a cylindrical sheath, and a flange through which the catheter passes. Before insertion, the sheath begins at a first opening near the catheter tip and extends into the catheter to a first circumferential fold, then back towards the catheter tip to a second circumferential fold about the tip to the exterior surface, and ends at a second opening attached to the flange. As the device is inserted up to a length, the flange abuts the cavity opening, and a corresponding length of the sheath deploys from the catheter interior, around the first and second circumferential folds, to the catheter outer surface. Once fully inserted, all, or a substantial portion, of the sheath initially positioned within the catheter has been deployed to the outer surface, thereby forming a protective barrier between the catheter and the surrounding tissues.

4 Claims, 3 Drawing Sheets

DEVICE FOR CLEAN CATHETERIZATION

CROSS-REFERENCES TO RELATED INVENTIONS

This application claims the benefit of prior-filed provisional application 63/177,505, Confirmation Number 1095, entitled, "Device for Sterile Catheterization," filed on Apr. 21, 2021.

FIELD OF THE INVENTION

The present invention is generally related to medical devices, and, more particularly, to a device for clean catheterization of an individual's bladder via the urethra.

STATEMENTS AS TO THE RIGHTS TO INVENTIONS MADE UNDER FEDERALLY SPONSORED RESEARCH OR DEVELOPMENT

Not applicable.

REFERENCE TO A "SEQUENCE LISTING," A TABLE, OR A COMPUTER PROGRAM LISTING APPENDIX SUBMITTED ON A COMPACT DISK

Not applicable.

BACKGROUND OF THE INVENTION

Every day, millions of people across the globe are unable to empty their bladders without the use of an external device to facilitate the drainage of urine. These individuals may experience bladder retention for a myriad of reasons, including: obstruction, weakened bladder muscles, certain medications, or nerve malfunction resulting from such conditions as stroke, tumor, diabetes, multiple sclerosis, Parkinson's Disease, and spinal cord injury. Thus, in order to urinate, these individuals rely on a catheter—a thin hollow tube inserted through the urethra into the bladder, through which urine is then discharged from the body.

It is estimated that 1.1 million Americans—and 10.8 million people globally—are catheterized daily in order to properly evacuate their bladders. Such catheterization, sometimes referred to as "clean intermittent catheterization" ("CIC"), requires an individual to insert a catheter through his or her urethra into the bladder periodically throughout the day in order to urinate. After cleaning the area around the urethral opening, the individual removes a catheter from its packaging and must take great care to keep the device clean before insertion to avoid the risk of infection, such as a urinary tract infection ("UTI").

Individuals who self-catheterize face a significantly increased risk for contracting a UTI for several reasons. First, bacteria present at the tip of the urethra (i.e., the urethral opening), such as may be present if the opening is not sufficiently cleaned or sterilized prior to insertion, can be dragged into the inner surface of the urethra and into the bladder. Second, improper handling of the catheter prior to insertion can result in contamination of the outer surface of the device, which is then introduced to the inner surface of the urethra and the bladder as the device is inserted. Finally, shear stress generated from the insertion of the catheter can result in tissue damage along the inner surface of the urethra, which may also lead to a UTI. It is estimated that self-catheterizing individuals face an increased risk of 40% to 60% annually of contracting a UTI.

This increased risk not only presents a challenge to the health of individuals performing CIC, but also to health care and insurance providers, as the costs of treating catheter-induced UTI's in self-catheterizing patients can far eclipse the costs of the catheters themselves. For example, an individual who performs CIC, using 4-6 catheters per day, each having a cost of $1.50 each will typically require approximately $3,240 per year in catheter costs. But the cost of treating a UTI can reach over $10,000—over three times the cost of the catheters themselves.

Currently available devices for self-catheterization attempt to mitigate the introduction of bacteria into the inner surface of the urethra and the bladder through the use of a protective bag or sheath positioned around the hollow tube of the catheter device. However, such devices are still at risk of introducing exterior contamination if the bag or sheath is touched or otherwise contaminated prior to insertion, they do not protect against the introduction of bacteria that may be present at the urethral opening by dragging or translocation, and they damage urethral tissue due to shear stress upon insertion.

Moreover, while certain currently available devices may include a catheter and a protective membrane deployed from therein as the device is inserted, such devices do not provide the desired protection from potential contamination present on the body of the catheter, or from contamination of the external environment from media passing through the catheter, such as urine leaking therefrom. For example, U.S. Pat. No. 5,897,535 by Felanzi and Jaker discloses a "non-contaminating probe" describes a device featuring a catheter and a protective membrane initially loaded within said catheter. As the device is inserted into a body cavity or canal, such as a urethra, the membrane is drawn out of the leading tip of the catheter and folded back around the surface of the catheter. However, the device disclosed by Felanzi and Jaker does not prevent the accidental removal of the membrane from the tip of the device, thereby exposing the surrounding tissues, such as the bladder or urethral wall, to contaminants present on the outer surface of the catheter. In fact, the device disclosed by Felanzi and Jaker is expressly configured for the eventual removal of the membrane once catheterization is complete.

It is therefore an object of the present invention to provide a device for clean catheterization capable of maintaining the sterility of a protective sheathing while simultaneously blocking or limiting the introduction of bacteria present at the urethral opening and/or on the outer surface of the catheter upon insertion of said device. It is a further object of the present invention that said sheathing be configured to reduce or eliminate shear stress upon insertion to protect against tearing the delicate tissues on the inner surface of the urethra during insertion of the catheter, and to prevent contamination of the external environment from material, such as urine, leaking out of the leading tip of the device as it flows through the interior of the catheter. An additional object/benefit of the present invention is to allow individuals with limited dexterity to grab the body of the catheter with gross motor movement without concern for contamination, thus allowing people who may not normally be able to self-catheterize the independence to do so without a caretaker.

SUMMARY OF THE INVENTION

According to an exemplary embodiment of the present invention, a device for clean catheterization may include a hollow, cylindrical catheter member having an outer surface, an inner surface defining a cavity, a base, and a tip. Said device may further comprise a flexible, hollow, sterilized or clean cylindrical sheath member having a first opening and a second opening. Said device may further comprise a flange member having an opening and configured such that said cylindrical catheter member passes through said flange opening. The flange member may have many configurations, depending upon the device use and/or intended user. For example, in some embodiments, the flange member may be a thin shape, such as a circle, oval, or any other shape, configured solely to act as a barrier between a user's hand and the sheath member. In other embodiments, the flange may be further configured to also act as a handle or grip for a user, and thus may be configured to have an appropriate shape, size, and surface texture to accommodate a human hand, such as a cylindrical grip. In its initial configuration (i.e., before insertion of the device into a body cavity, such as a urethra), the device may be configured such that a first portion of the sheath member is positioned inside of the cavity of the catheter member, and a second portion of said sheath member is positioned outside of the catheter member such that the sheath member folds back around the tip of the catheter member such that said second portion covers a portion of the outer surface of the catheter member extending from the tip back towards the base, and the second opening of the sheath member makes contact with the flange member. In certain embodiments, the sheath member may be configured to attach to the flange member at the second opening, but in other embodiments, the sheath member merely contacts said flange member without being attached thereto. Similarly, in certain embodiments of the present invention, the sheath member may attach to the inner surface of the catheter member such that the first opening of said sheath member attaches to the inner surface of said catheter member inside the tip of the catheter member. The sheath member may also attach to the body of said catheter member outside the tip on the segment that is covered by the portion of the sheath that is folded back on the outside. This may allow for future versions that include a balloon in the catheter body for indwelling catheters.

Certain embodiments of the present invention may further include a handle member, such that the base of the catheter member is configured to receive said handle member, which may be configured to be gripped by a user, and further configured to prevent the flow of liquid out of the catheter member through the base until said handle member is opened or removed. The device may be further configured such that a user handles said device only on the base side of the flange member, thereby avoiding any contact with the clean and/or sterile sheath member. The device may be further configured such that the base of the catheter attaches to a bag or container configured for fluid collection.

As the device is placed into position to be inserted into a body cavity, such as a urethra, the device may be configured such that the flange member abuts the cavity opening. As the device is inserted up to a length, the device may be further configured such that an equal length of the first portion of the sheath member position inside of the cavity member is deployed out of the tip of the catheter member such that said length of the first portion folds back around said tip to the outer surface of the catheter member, thereby feeding into the second portion of the sheath member along the outer surface of the catheter member. Accordingly, the device may be configured such that, as it is inserted up to said length, a corresponding length of clean sheath member positioned inside of the catheter cavity is deployed out and around the outer surface of the catheter member. The device may be further configured to prevent the introduction of bacteria present at or around the cavity opening into said cavity through the introduction of only clean sheath material from inside of the catheter cavity.

DETAILED DESCRIPTION

Figure 1:
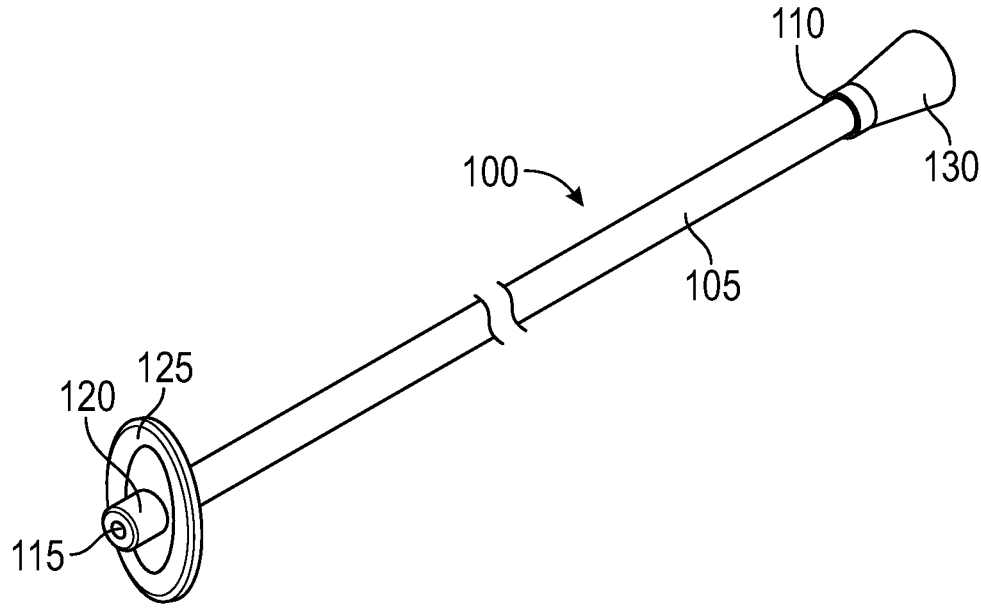
FIG. 1 is an isometric exterior view of a device for clean catheterization, according to an exemplary embodiment of the present invention.
Figure 2:
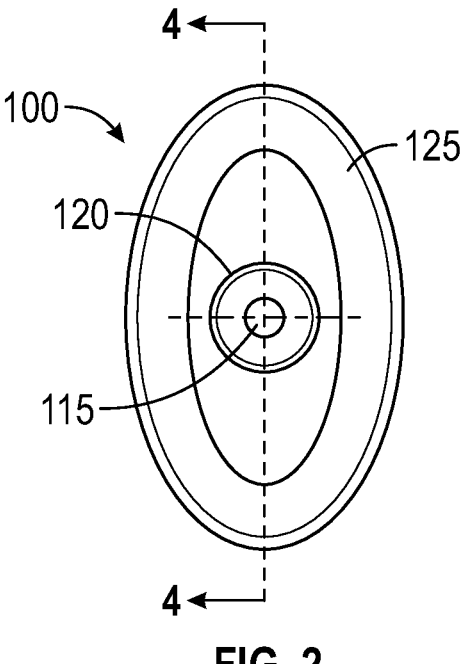
FIG. 2 is a front view exterior of a device for clean catheterization, according to an exemplary embodiment of the present invention.
Figures 3, 4:
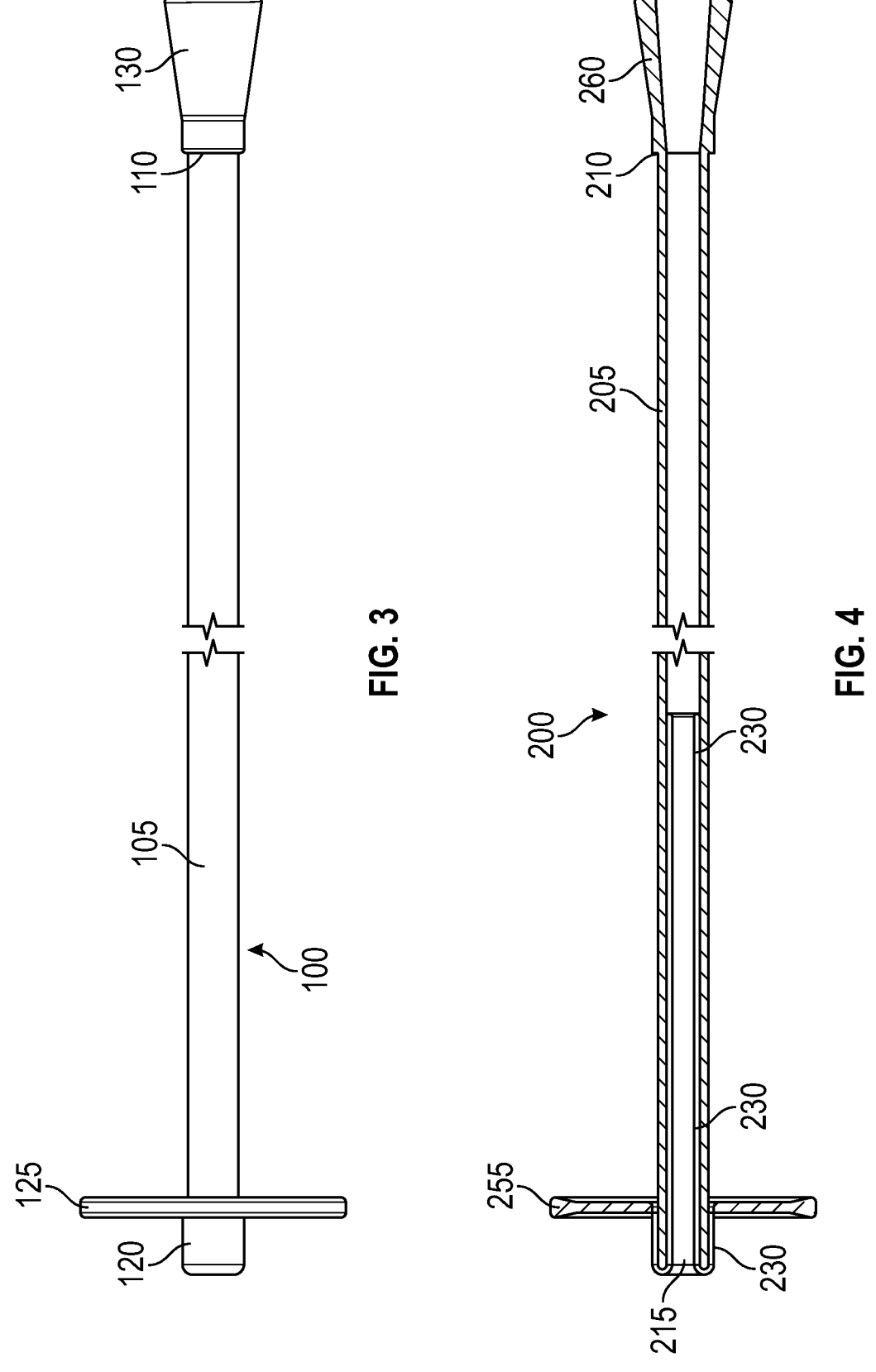
FIG. 3 is a side exterior view of a device for clean catheterization, according to an exemplary embodiment of the present invention.
FIG. 4 is a side cross-section view of a device for clean catheterization, according to an exemplary embodiment of the present invention.

FIGS. 1, 2, and 3 are isometric, front, and side external views, respectively, of a device 100 for clean catheterization according to an exemplary embodiment of the present invention. Said device 100 may comprise a catheter member 105 having a base 110 and a tip 115, a sheath member 120, a flange member 125, and a handle member 130. Sheath member 120 may be comprised of any flexible material such that a first portion of said sheath member 120 is positioned inside of catheter member 105, with a second portion of said sheath member 120 extending out of tip 115 and back around catheter member 105 such that it makes contact with flange member 125, which is configured such that said catheter member 105 passes through an opening in flange member 125. In preferred embodiments, sheath member 120 may be attached to flange member 125, but in others, sheath member 120 merely makes contact with flange member 125. Base 110 may be configured to receive handle member 130, which may be configured to be gripped by a user. In certain embodiments, handle member 130 may be further configured to prevent the flow of liquid out of catheter member 105 through base 110 until handle member 130 is opened or removed.

Sheath member 120 may be further configured to be biocompatible, clean, and/or sterile. In further embodiments of the present invention, sheath member 120 may be a urethane, a silicone, a polyvinyl, or any other similar material. Sheath member 120 may be further configured to have a Young's modulus of elasticity from about 1.32 to about 2.97 MPa. Sheath member 120 may be further configured to minimize friction to the interior of a body cavity into which the device is inserted in order to prevent injury to surrounding tissues.

As it is moved into position for insertion into a body cavity, such as a urethra, device 100 may be configured such that flange member 125 abuts the cavity opening, and further configured such that a user handles device 100 on the base-facing side of flange member 125, thereby preventing contact with, and contamination of, sheath member 120.

According to an exemplary embodiment of the present invention, as device 100 is inserted into said cavity up to a given length, a corresponding length of sheath member 120 is deployed from inside of catheter member 105 such that it wraps around tip 115 to the outer surface of catheter member 105 extending in the direction opposite the direction of insertion, towards base 110.

Figure 5:
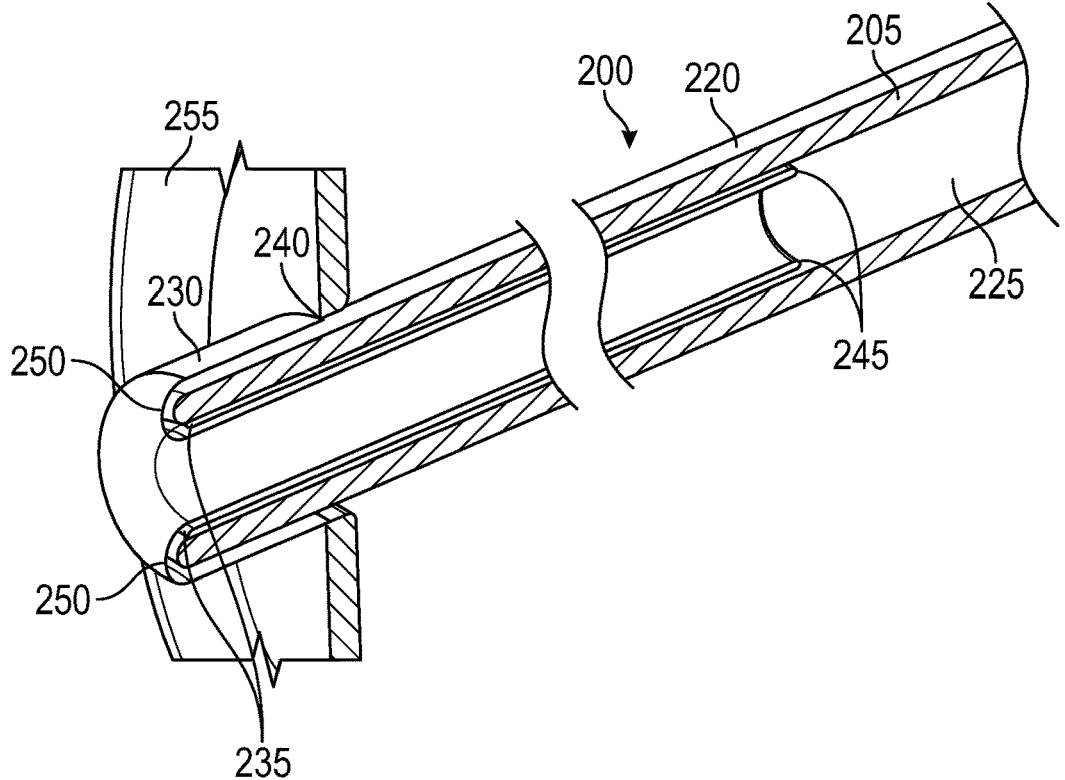
FIG. 5 is an isometric cross-section view of a device for clean catheterization, according to an exemplary embodiment of the present invention.

FIGS. 4 and 5 are side and isometric cross-section views, respectively, of a device 200 for clean catheterization according to an exemplary embodiment of the present invention. Said device may further comprise a hollow catheter member 205 having a base 210, a tip 215, an outer surface 220, and an inner surface 225; a sheath member 230 having a first opening 235, a second opening 240, a first circumferential fold 245, and a second circumferential fold 250; a flange member 255; and a handle member 260. Said flange member 255 may be configured such that said catheter member 205 passes through an opening in flange member 255. Device 200 may be further configured such that sheath member 205 comprises three portions: a first portion extending from first opening 235 to first circumferential fold 245, a second portion extending from first circumferential fold 245 to second circumferential fold 250, and a third portion extending from second fold 250 to second opening 240. Thus, in certain embodiments, device 200 may be configured such that: said first portion of sheath member 230 extends along inner surface 225 of catheter member 205 from tip 215 to first circumferential fold 245 such that the outer surface of sheath member 230 faces or contacts inner surface 225 of catheter member 205 along the length of said first portion. At first circumferential fold 245, sheath member 230 may double back in the direction of tip 215, thereby defining said second portion of sheath member 230 extending from first circumferential fold 245 back towards second circumferential fold 250 at tip 215. At second circumferential fold 250, sheath member 230 may fold from the inner surface 225 of catheter member 205 to outer surface 220, thereby defining said third portion of sheath member 230 extending along the outer surface 225 from tip 215 toward flange 255, wherein second opening 240 of sheath member 230 terminates at flange member 255.

As it is moved into position for insertion into a body cavity, such as a urethra, device 200 may be configured such that flange member 255 abuts the cavity opening, and further configured such that a user handles device 200 on the base-facing side of flange member 255, thereby preventing contact with, and contamination of, sheath member 230. According to an exemplary embodiment of the present invention, as device 200 is inserted into said cavity up to a given length, a corresponding length of said first portion of sheath member 230 feeds into said second portion of sheath member 230, then from said second portion of sheath member 230 into said third portion of said sheath member 230, such that a corresponding length of sheath member 230 is deployed from inside of catheter member 205 such that it wraps around tip 215 to outer surface 220 of catheter member 205 extending in the direction opposite the direction of insertion, towards base 210.

According to an exemplary embodiment of the present invention, sheath member 230 may have a second opening 240 terminating at flange member 255, and a first opening 235 which may terminate either on the interior surface 225 or exterior surface 220 of catheter 205. Thus, in certain embodiments, first opening 235 may terminate at a location on the interior surface 225 of catheter 205 just within the opening of tip 215 as illustrated in FIG. 5, or, in other embodiments, first opening 235 may terminate on the outer surface 220 of catheter 205 at a location towards flange 255. In further embodiments of the present invention, said first opening 235 of sheath member 230 may be fused with or otherwise attached to catheter 205 at said locations either on the inner surface 225 or on the outer surface 230 of catheter 205. In a preferred embodiment of the present invention, catheter member 205 and sheath member 230 are manufactured as a single, continuous piece consisting of both lumen (catheter member 205) and protective sheath member 230. Therefore, according to said preferred embodiment of the present invention, once device 200 has been fully inserted into a body cavity such that substantially all of sheath member 230 has been deployed from the interior of catheter 205 to the exterior surface 220 of catheter 205 such that said first portion and said second portion and circumferential fold 245 have been eliminated, the joining of sheath member 230 to catheter member 205 at first opening 235 prevents exposure—accidental or otherwise—of outer surface 220 to surrounding tissues of said body cavity. Thus, sheath member 230 remains in place, completely encompassing the length of outer surface 220 that has been inserted into said body cavity. Moreover, said joining of sheath member 230 to catheter member 205 at first opening 235 further prevents leakage from tip 215 of any liquid—such as urine—flowing through inner surface 225 after device 200 is in place, as said liquid will be prevented from exiting tip 215 due to the fusion and/or connection of sheath member 230 to catheter 205 at first opening 235.

Sheath member 230 may be further configured to be biocompatible and clean/sterile. In further embodiments of the present invention, sheath member 230 may be a urethane, a silicone, a polyvinyl, or any other similar material. Sheath member 230 may be further configured to have a Young's modulus of elasticity from about 1.32 to about 2.97 MPa. Sheath member 230 may be further configured to minimize friction to the interior of a body cavity into which the device is inserted in order to prevent injury to surrounding tissues. In further embodiments, handle member 260 may be further configured to be gripped by as to support device 200 during insertion. Handle member 260 may be further configured to stop the flow of liquid out of catheter member 205 out of base 210 until handle member 260 is removed or opened. Moreover, in some embodiments of the present invention, inner surface 225 may be configured such that said first portion of sheath member 230 (i.e., the portion beginning at first opening 235 and extending to first circumferential fold 245) is loosely adhered to inner surface 225 in order to accomplish a controlled deployment of sheath member 230 from within catheter 205 as the device is inserted into a body cavity in order to prevent the folded sheath member 230 from sliding out of tip 215 before or during insertion. Thus, inner surface 225 may be configured such that said first portion of sheath member 230 adheres to inner surface 225 enough to prevent inadvertent slippage of said first portion out of catheter 205, but not so strongly as to prevent deployment of said first portion as the device is inserted during catheterization. Such adherence may be accomplished by a static electric charge between inner surface 225 and said first portion, texturing inner surface 225 in a manner configured to increase friction between inner surface 225 and said first portion, an adhesive applied to inner surface 225, or other similar means known in the art.

Figure 6:
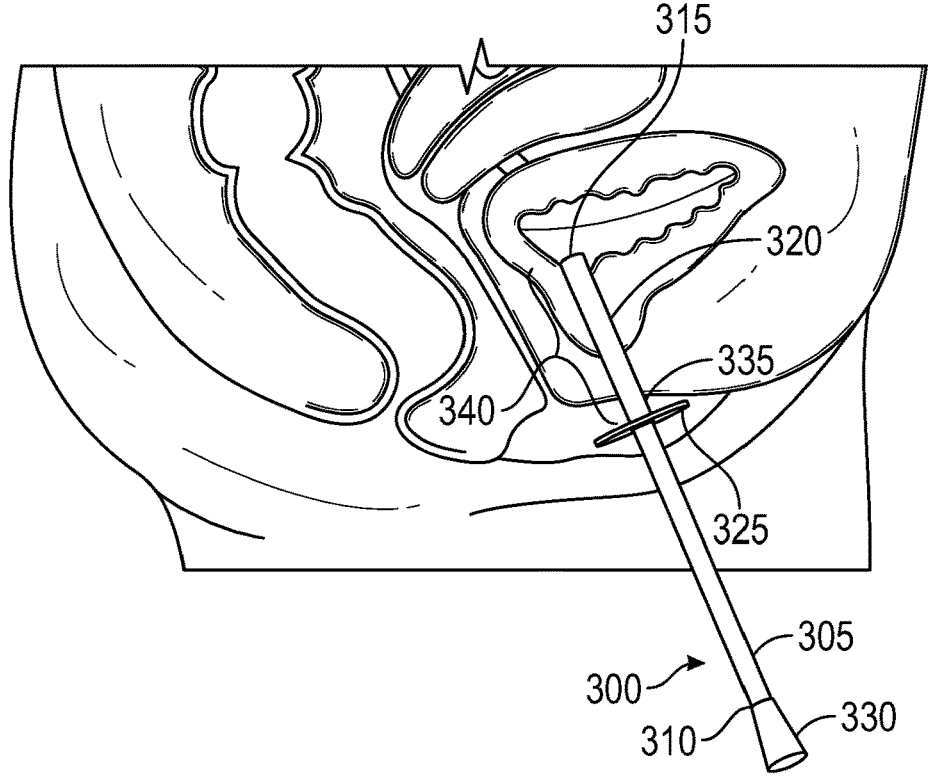
FIG. 6 is a side view of a device for clean catheterization, according to an exemplary embodiment of the present invention, being deployed through a urethra into a bladder.

FIG. 6 is a side view of a device 300 for clean catheterization according to an exemplary embodiment of the present invention. Said device 300 may comprise a catheter member 305 having a base 310 and a tip 315, a sheath member 320, a flange member 325, and a handle member 330. Sheath member 320 may be comprised of any clean, biocompatible, flexible material and configured such that a first portion of said sheath member 320 is positioned inside of catheter member 305, with a second portion of said sheath member 320 extending out of tip 315 and back around catheter member 305 such that it makes contact with flange member 325. In certain embodiments, sheath member 320 may be attached to flange member 325. Base 310 may be configured to receive handle member 330, which may be configured to be gripped by a user.

As it is moved into position for insertion into a body cavity, such as urethra 335, device 300 may be configured such that flange member 325 abuts the exterior opening of urethra 335, and further configured such that a user handles device 300 on the base-facing side of flange member 325, thereby preventing contact with, and contamination of, sheath member 320. According to an exemplary embodiment of the present invention, as device 300 is inserted into urethra 335 up to length 340, a corresponding length of sheath member 320 is deployed from inside of catheter member 305 such that it wraps around tip 315 to the outer surface of catheter member 305 extending in the direction opposite the direction of insertion, towards base 310.

While the embodiments of the present invention are described herein with reference to various implementations and exploitations, it will be understood that these embodiments are illustrative and that the scope of the invention(s) is not limited to them. In general, embodiments of a device for separating tissue during dissection as described herein may be implemented using methods, facilities, devices, and materials consistent with any appropriate structure as described or illustrated herein. Many variations, modifications, additions, and improvements are possible.

For example, plural instances may be provided for components, operations, or structures described herein as a single instance. Boundaries between various components, operations, and functionality are depicted somewhat arbitrarily, and particular operations are illustrated within the context of specific illustrative configurations. In general, structures and actions presented as separate components or steps in the exemplary configurations may be implemented as a combined structure or step. Similarly, structures and actions presented as a single component or step may be implemented as separate components or steps. These and other variations, modifications, additions, and improvements may fall within the scope of the inventive subject matter.

What is claimed is:

1. A device for catheterization, comprising:

A singular hollow catheter member having a proximal end, a distal end, an outer surface, and an inner surface defining a cavity of the singular hollow catheter member;

a deployable cylindrical sheath member having a first opening, a second opening, a first portion extending from said first opening to a first circumferential inversion, a second portion extending from said first circumferential inversion to a second circumferential inversion, and a third portion extending from said second circumferential inversion to said second opening; and a flange member having an opening;

wherein said flange member is configured such that said singular hollow catheter member passes through the opening in said flange member;

wherein said second opening is attached to said flange member;

wherein said first opening of the cylindrical sheath is permanently circumferentially fused to the surface of said singular hollow catheter member at the proximal end of the singular hollow catheter member such that the cylindrical sheath prevents leakage of a liquid flowing through the cavity of the singular hollow catheter member from said proximal end;

wherein, prior to insertion of said device into a body cavity, said first portion of the sheath member begins at said first opening of the cylindrical sheath and extends axially within said cavity of the singular hollow catheter member in the direction of the distal end of the singular hollow catheter member to the first circumferential inversion;

said second portion of the sheath member begins at said first circumferential inversion and extends axially within said cavity of the singular hollow catheter member back towards the proximal end of the singular hollow catheter member to the second circumferential inversion about said proximal end; and said third portion of the sheath member begins at the second circumferential fold inversion as said sheath member folds around the proximal end to the outer surface of the singular hollow catheter member, and extends to said second opening of the cylindrical sheath thereby forming a continuous sterile barrier between a portion of the outer surface of said singular hollow catheter member and a surrounding environment;

wherein, as the device is inserted into said body cavity up to a length, said flange abuts the opening of said body cavity, a corresponding length of said first portion is deployed into said second portion, then from said second portion into said third portion encompassing a corresponding length of the outer surface of said singular hollow catheter member thereby maintaining the continuous sterile barrier between said length of the outer surface of the singular hollow catheter member and the surrounding environment; and wherein, upon complete insertion of said device into said body cavity, all of said first portion and said second portion have deployed into said third portion along the outer surface of said singular hollow catheter member.

2. The device of claim 1, wherein said sheath member and said singular hollow catheter member are manufactured as a single, continuous hollow member.

3. The device of claim 2, wherein said first opening is permanently circumferentially fused to the inner surface of said singular hollow catheter member.

4. The device of claim 3, wherein said first opening is permanently circumferentially fused to the outer surface of said singular hollow catheter member.

* * * * *